United States Patent
Miller et al.

(10) Patent No.: US 6,553,255 B1
(45) Date of Patent: Apr. 22, 2003

(54) USE OF BACKGROUND ELECTROLYTES TO MINIMIZE FLUX VARIABILITY DURING IONTOPHORESIS

(75) Inventors: David J. Miller, Bountiful, UT (US); Kevin Li, Salt Lake City, UT (US); William I. Higuchi, Salt Lake City, UT (US)

(73) Assignee: ACiont Inc., Salt Lake City, UT (US)

( * ) Notice: Subject to any disclaimer, the term of this patent is extended or adjusted under 35 U.S.C. 154(b) by 350 days.

(21) Appl. No.: 09/698,697

(22) Filed: Oct. 27, 2000

(51) Int. Cl.⁷ ................................................. A61N 1/30
(52) U.S. Cl. ............................ 604/20; 604/19; 604/21; 604/890.1; 604/501
(58) Field of Search ............................. 604/20, 890.1, 604/21, 19, 501, 500

(56) References Cited

U.S. PATENT DOCUMENTS

| | | |
|---|---|---|
| 4,250,878 A | 2/1981 | Jacobsen et al. |
| 4,383,529 A | 5/1983 | Webster |
| 4,474,570 A | 10/1984 | Ariura et al. |
| 4,702,732 A | 10/1987 | Powers et al. |
| 4,722,726 A | 2/1988 | Sanderson et al. |
| 4,744,787 A | 5/1988 | Phipps et al. |
| 4,747,819 A | 5/1988 | Phipps et al. |
| 4,752,285 A | 6/1988 | Petelenz et al. |
| 4,820,263 A | 4/1989 | Spevak et al. |
| 4,886,489 A | 12/1989 | Jacobsen et al. |
| 4,973,303 A | 11/1990 | Johnson et al. |
| 5,019,034 A | 5/1991 | Weaver et al. |
| 5,080,646 A | 1/1992 | Theeuwes et al. |
| 5,085,749 A * | 2/1992 | Grimshaw et al. ........ 204/182.1 |
| 5,125,894 A | 6/1992 | Phipps et al. |
| 5,135,477 A | 8/1992 | Untereker et al. |
| 5,135,478 A | 8/1992 | Sibalis |
| 5,302,172 A | 4/1994 | Sage, Jr. et al. |
| 5,322,520 A * | 6/1994 | Milder ........................ 604/265 |
| 5,328,452 A | 7/1994 | Sibalis |
| 5,328,455 A | 7/1994 | Llyod et al. |
| 5,374,242 A | 12/1994 | Haak et al. |
| 5,391,195 A | 2/1995 | Van Groningen |
| 5,421,817 A | 6/1995 | Liss et al. |
| 5,466,350 A * | 11/1995 | Baker et al. ........... 204/153.14 |
| 5,685,837 A * | 11/1997 | Horstmann .................. 604/20 |
| 5,771,890 A | 6/1998 | Tamada et al. |
| 5,850,242 A * | 12/1998 | Asaba ......................... 347/59 |
| 5,865,792 A * | 2/1999 | Ledger et al. ................ 604/20 |
| 5,882,677 A * | 3/1999 | Kupperblatt ................ 424/449 |
| 5,968,006 A | 10/1999 | Hofmann |
| 5,983,130 A * | 11/1999 | Phipps et al. ................. 604/20 |
| 5,985,316 A * | 11/1999 | Gyory et al. ................ 424/449 |
| 6,023,629 A | 2/2000 | Tamada et al. |
| 6,049,733 A | 4/2000 | Phipps et al. |
| 6,350,259 B1 * | 2/2002 | Sage, Jr. et al. ............. 604/501 |

OTHER PUBLICATIONS

Deen (1987), "Hindered Transport of Large Molecules in Liquid–Filled Pores," *AIChE Journal* 33(9):1409–1425.
Tamada, et al. (1999), "Noninvasive Glucose Monitoring—Comprehensive Clinical Results," *JAMA* 282(19):1839–1844.

* cited by examiner

Primary Examiner—Ira S. Lazarus
Assistant Examiner—Tu Cam Nguyen
(74) Attorney, Agent, or Firm—Reed & Eberle LLP

(57) ABSTRACT

A device and method are provided that minimize the changes in flux encountered during iontophoresis and reduce inter-subject variability. For drug delivery, the active agent to be delivered is administered in conjunction with at least one background ion having a hindrance factor that changes at a faster rate than the hindrance factor of the active agent when an electrical current is applied. For analyte extraction, the extraction reservoir contains at least one background ion having a hindrance factor that changes at a faster rate than the hindrance factor of the background ions of the analyte in the tissue when an electrical current is applied.

89 Claims, 6 Drawing Sheets

Schematic diagram of iontophoretic transport. The negative charges on the pore walls cause cations such as sodium ions ($Na^+$) to be transported from the anode to the cathode. Conversely, drug ions ($D^-$) and background ions (also known as co-ions, $X^-$) move from the cathode to the anode. In this figure, the anode is defined as the electrode with the positive polarity at one instant in time and the cathode is the electrode with the negative polarity at that same instant in time. The use of the terms anode and cathode should not be construed to mean these electrodes are of fixed polarity and therefore, represent DC current.

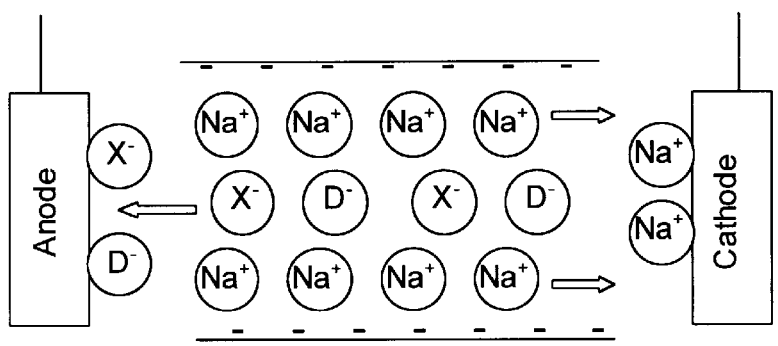

Figure 1a. Schematic diagram of iontophoretic transport. The negative charges on the pore walls cause cations such as sodium ions ($Na^+$) to be transported from the anode to the cathode. Conversely, drug ions ($D^-$) and background ions (also known as co-ions, $X^-$) move from the cathode to the anode. In this figure, the anode is defined as the electrode with the positive polarity at one instant in time and the cathode is the electrode with the negative polarity at that same instant in time. The use of the terms anode and cathode should not be construed to mean these electrodes are of fixed polarity and therefore, represent DC current.

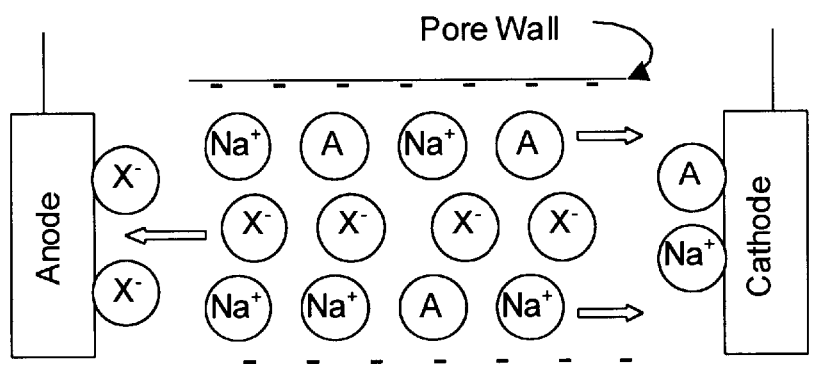

Figure 1b. Schematic diagram of iontophoretic transport for analyte extraction. The negative charges on the pore walls cause the co-ion of the analyte (such as $Na^+$) to be transported from the anode to the cathode. Conversely, background anions ($X^-$) move from the cathode to the anode. In this instance, an uncharged or positively charged analyte (A) moves from the anode to the cathode.

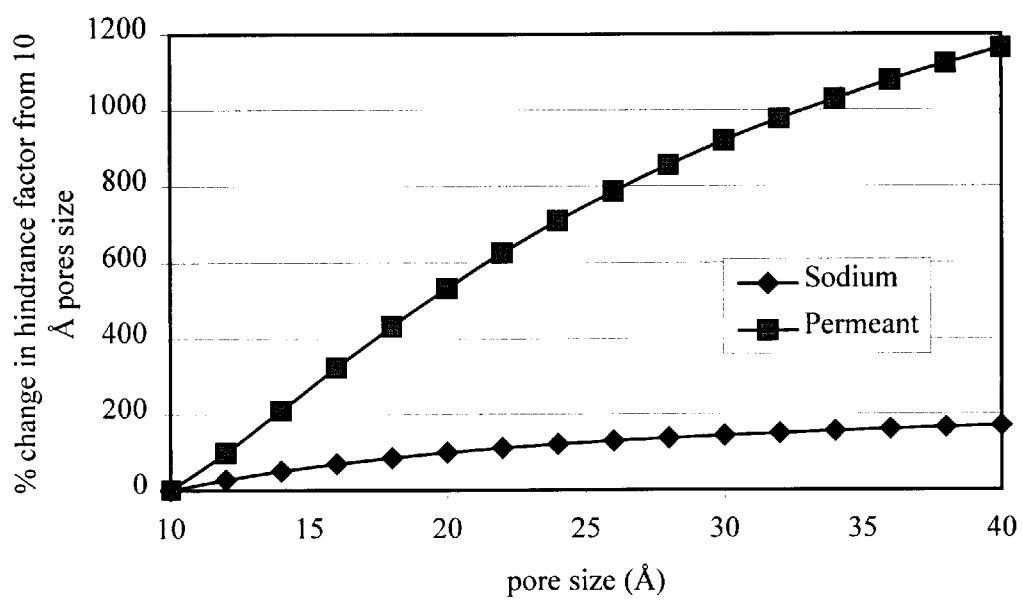
Figure 2. Calculated change in hindrance factor for the permeant and sodium ion as a function of changing pore size from 10 to 40 Angstroms. Assumptions made are that the radius of $Na^+$ is 2.5 Å compared with 5.0 Å for the permeant and that the permeant has a charge of -1.

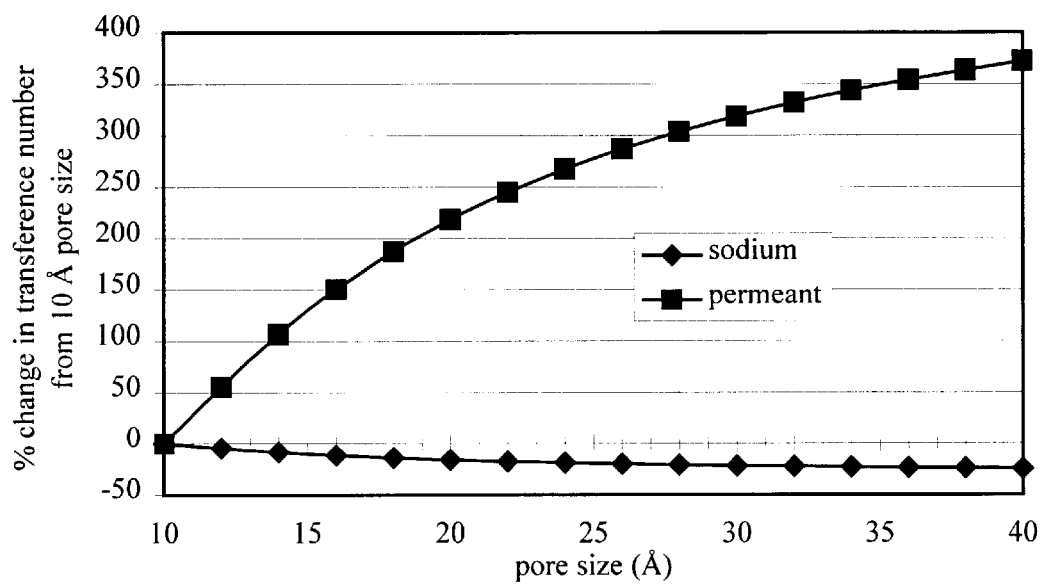
Figure 3. Calculated change in transference number for the permeant and sodium ion as a function of changing pore size from 10 to 40 Å. Assumptions made are that the radius of $Na^+$ is 2.5 Å compared with 5 Å for the permeant and that the permeant has a charge of -1. Also, the diffusivities of sodium and the permeant are 2.0 and 1.2 $cm^2/s$ respectively.

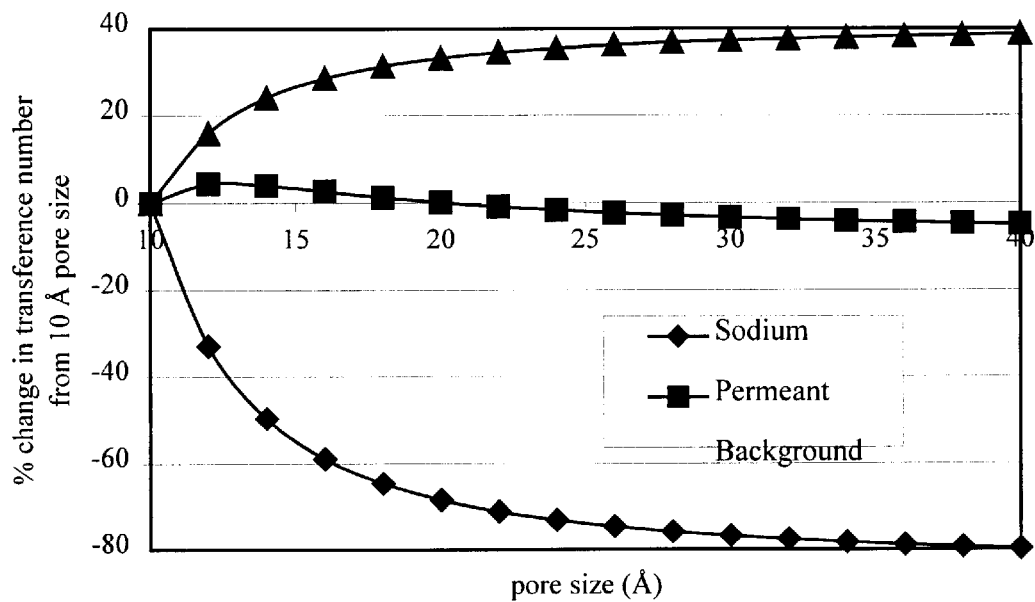

Figure 4. Calculated change in transference number for the permeant, background electrolyte, and sodium as a function of changing pore size from 10 to 40 Å. Assumptions made are that the radii of sodium ion, permeant ion, background electrolyte are 2.5, 5, and 7 Å respectively, the solution concentrations are 0.1, 0.001, and 0.02 M respectively, and the bulk diffusivities are 2.0, 1.2, and 0.43 x $10^{-5}$ cm$^2$/sec respectively.

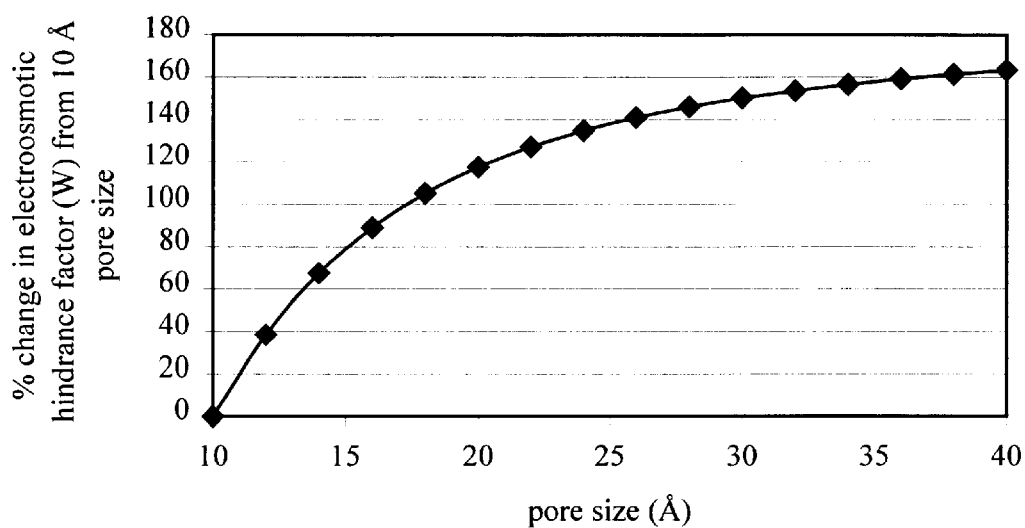
Figure 5. Calculated percent change in electroosmotic flow hindrance with respect to pore size using Eq. 12 and a permeant radius of 5 Å.

USE OF BACKGROUND ELECTROLYTES TO MINIMIZE FLUX VARIABILITY DURING IONTOPHORESIS

TECHNICAL FIELD

This invention relates generally to the use of iontophoresis for permeant transport and, more specifically, to a method and device capable of reducing variability in the iontophoretic process by the use of a background co-ion that minimizes changes in the permeant flux and reduces intertissue variability.

BACKGROUND

Iontophoresis is commonly defined as the introduction of a compound or composition into the body or across a tissue by means of an electric current although; recently reverse iontophoresis has been used to non-invasively withdraw analytes (e.g. glucose) through the patient's skin for analysis. In practice, transdermal iontophoresis is a non-invasive method of enhancing the passage of drugs or other compounds across the skin or mucosal tissue. Unfortunately, most iontophoretic methods cannot provide a constant flux at constant current, likely due to time-dependent changes in the porosity (permeability) of the skin, changes in the surface charge density, and changes in the effective pore size of the pathways in skin during the course of iontophoresis. The inability to adequately predict and control permeant transport has severely limited clinician, patient, industry, and regulatory authority acceptance of iontophoresis as a viable drug delivery or analyte extraction option.

Systems for transporting ionized substances through the skin have been known for some time. British Patent Specification No. 410,009 (1934) describes an iontophoretic delivery device that overcame one of the disadvantages of the early devices, namely, the need to immobilize a patient near a source of electric current. The device was made by forming a galvanic cell which itself produced the current necessary for iontophoretic delivery from the electrodes and the material containing the drug to be delivered. Unlike previous iontophoretic delivery systems, the device allowed the patient to move around during drug delivery and thus minimized interference with the patient's daily activities.

In present iontophoretic devices, at least two electrodes are used. Both of these electrodes are disposed so as to be in intimate electrical contact with some area of the body surface, i.e., skin or mucosal tissue. In iontophoretic drug delivery, one electrode, called the active or donor electrode, is the electrode from which the drug is delivered into the body. The other electrode, called the counter or return electrode, serves to close the electrical circuit through the body. If the ionic substance to be driven into the body is positively charged, then the positive electrode (the anode) will be the active electrode and the negative electrode (the cathode) will serve as the counter electrode, completing the circuit. If the ionic substance to be delivered is negatively charged, then the cathode will be the active electrode and the anode will be the counter electrode.

In analyte extraction, the electrode that receives the analyte from the body can be termed the receiver electrode and the second electrode can be termed the indifferent or return electrode. If the substance being extracted from the body is a cation (positively charged), the receiver electrode will be the cathode. Conversely, if the extracted substance is an anion, the anode will be the receiver electrode. If, however, the extracted substance is uncharged, the receiver electrode will be the cathode because of the direction of electroosmotic flux in the direction of anode to cathode under physiological conditions.

In conjunction with the patient's skin, the circuit is completed by connection of the electrodes to a source of electrical energy, e.g., a battery, and usually to circuitry capable of controlling current passing through the device.

Iontophoretic drug delivery devices also generally include a reservoir or source of the drug that is to be delivered into the body. Iontophoretic analyte extraction devices include a reservoir for collection of the analyte. Examples of such reservoirs or sources include a pouch, as described in Jacobsen, U.S. Pat. No. 4,250,878, a pre-formed gel body, as disclosed in Webster, U.S. Pat. No. 4,382,529 and Ariura et al. U.S. Pat. No. 4,474,570, a receptacle containing a liquid solution, as disclosed in Sanderson, et al., U.S. Pat. No. 4,722,726, a wetable woven or non-woven fabric, a sponge material, or any combination thereof. Such reservoirs are connected to the anode or the cathode of an iontophoretic device to provide a fixed or renewable source of one or more desired agents.

It is known that during direct current (DC) iontophoresis, the applied current causes pores in the skin cells to form (electroporation) and enlarge resulting in reduced electrical resistance. In addition, the direct current changes the net charge density of the pores. See, for example, U.S. Pat. No. 5,374,242 to Haak et al. and U.S. Pat. No. 5,019,034 to Weaver et al. Electroporation does not itself affect permeant transport but merely prepares the tissue thereby treated, for delivery of a drug by any of a number of techniques, one of which is iontophoresis.

In existing iontophoresis devices, the amount of agent transported across the tissue through these pores, generally referred to as the "flux", varies with time during the course of a typical iontophoresis procedure. Serious variability in the permeant flux exists during the first one to two hours of the application. The flux drift can then stabilize or continue to change depending on the permeant transported, the current profile, excipients present in the formulation, and the status of the biological membrane through which transport occurs. Intra- and inter-patient variability is also a major concern in iontophoretic devices, due to differences in the pores from one area of tissue to the next or from one patient to the next. In addition, different regions of a patient's skin or skin between different patients respond differently to the electrical current, with some skin changing more than others. Some of the factors influencing the change in pore size are the patient's age, level of hydration of the stratum corneum, previous damage, follicular density, or other unknown factors.

The variability in permeant flux during iontophoresis is the main complication accompanying pore induction (electroporation) in human skin at low to moderate voltages. Since the amount of material (e.g., drug delivery or analyte extraction) transported across skin varies with time, varies among patients, and varies from day-to-day in the same patient, controlled and predictable permeant transport using iontophoresis has heretofore not been possible.

As stated in U.S. Pat. No. 5,983,130 to Phipps et al., it has been recognized in the art that "competitive" ionic species having the same charge (i.e., the same sign) as the drug ions being delivered by electrotransport compete with the permeant ion for the electrical current and therefore have a negative impact on electrotransport efficiency. For example, Untereker et al., U.S. Pat. No. 5,135,477 and Petelenz et al., U.S. Pat. No. 4,752,285 state that competitive ionic species are electrochemically generated at both the anode and cathode of an electrotransport delivery device and present methods for reducing the negative effects of these competitive ionic species using cation permeants in the form of salts.

In addition, formulation excipients can provide extraneous competing ions. Some devices employ sodium chloride as a chloride source to control the migration of silver ions formed at a silver foil cathode. U.S. Pat. No. 6,049,733 to Phipps et al. teaches the use of supplementary chloride ion sources in the form of high molecular weight chloride resins in the donor reservoir of a transdermal electrotransport device. The resins are highly effective at providing sufficient chloride to capture the competitive silver ion and prevent their migration, yet because of the high molecular weight of the resin cation, the resin cation is effectively immobile and hence cannot compete with the permeant for transport through the body surface.

Competing co-ions have also been used to dampen transport efficiency in U.S. Pat. No. 5,983,130 to Phipps et al. However, the method of the patent is focused on biocompatible salts as co-ions that are used in quantities sufficient to raise the total current density above a critical current density at which the skin attains a highly transmissive state. Additionally, the Phipps patent makes reference to the disclosure of U.S. Pat. No. 5,080,646 to Theeuwes et al., stating that this reference provides sufficient teaching for one skilled in the art to select a suitable quantity and species of competitive co-ion to be transported along with the permeant. While Theeuwes et al. does contain a mathematical analysis of the effects of a hydrophilic resin within a hydrophobic matrix, it is silent as to the impact of electroporation-induced flux variability and the use of co-ions having hindrance factors that change at a faster rate than the hindrance factor of the permeant. As a consequence, neither Phipps et al. nor Theeuwes et al. provide a method or device that is capable of stabilizing permeant flux and reducing intra- and inter-patient variability.

Uncharged permeants also face inter- and intra-tissue, pore size change induced variability during iontophoretic extraction. For example, U.S. Pat. Nos. 6,023,629 and 5,771,890 both to Tamada, et. al., discuss the need for normalizing the flux drift of glucose during DC iontophoresis. The drift in flux requires a complicated algorithm to correlate extracted glucose with blood glucose. In Tamada, et al. (*JAMA*;282(19):1839–1844, 1999), the authors describe the algorithm needed to obtain reasonable correlation between blood glucose and extracted glucose using a mixture of experts method with input variables of the biosensor signal, the blood glucose value at calibration; the elapsed time since calibration, and an electrically derived offset. The algorithm was established based on population statistics. Therefore, if the patient's skin parameters change outside of population norms, the glucose extraction device will give an ever increasingly incorrect reading as time of analysis progresses. Such drifts in flux necessitate the current art to have frequent, painful calibrations and an imprecise algorithm to decrease inaccuracy due to these well-known flux-drifts. There is, therefore, a need in the art for a method and device that address these concerns. The present invention provides a method and an apparatus that incorporates background ions having a hindrance factor that changes at a faster rate than the hindrance factor of the permeant during iontophoresis and stabilizes iontophoretic flux. It is proposed that the change in the hindrance factor will stabilize the transference number for reasons discussed infra.

SUMMARY OF THE INVENTION

In one main aspect of the current invention, a drug delivery device is provided that minimizes changes in iontophoretic flux and reduces intertissue variability that is comprised of (a) a first electrode assembly adapted to be placed in agent-transmitting relation with a body tissue that contains a pharmacologically active agent to be delivered and at least one background co-ion that has a hindrance factor that changes at a faster rate than the hindrance factor of the active agent when an electrical current is applied; (b) a second electrode assembly, adapted to be placed in ion transmitting relation with the body surface at a location spaced apart from the first electrode assembly; and (c) an electrical current source, electrically connected to the first and second electrode assemblies.

In another aspect of the invention, a method for delivering a pharmacologically active agent across body tissue using electrical current is provided, the improvement comprising co-delivering with the active agent at least one background co-ion having a hindrance factor that changes at a faster rate than the hindrance factor of the active agent when an electrical current is applied. The presence of the background co-ion minimizes changes in active agent flux and reduces intertissue variability.

In yet another aspect of the invention, a method for delivering a pharmacologically active agent across a region of body tissue is provided. First, a composition comprising the pharmacologically active agent and at least one background co-ion is placed in contact with the body tissue. The background electrolyte has a hindrance factor that changes at a faster rate than the hindrance factor of the active agent when an electrical current is applied and therefore becomes an ever-increasing competitor for the electrical current as the pore size enlarge. Second, an electrical current of a voltage and duration effective to induce electroporation is applied to the region of body tissue.

In a second main aspect of the invention, an analyte extraction device is provided that minimizes changes in iontophoretic flux and reduces intertissue variability that is comprised of (a) a first electrode assembly adapted to be juxtaposed with a body tissue that contains a reservoir for analyte collection and at least one background electrolyte that has a hindrance factor that changes at a faster rate than the hindrance factor of the transporting co-ion to the analyte in the body or tissue system when an electrical current is applied; (b) a second electrode assembly, adapted to be placed in ion transmitting relation with the body surface at a location spaced apart from the first electrode assembly; and (c) an electrical current source, electrically connected to the first and second electrode assemblies.

In another aspect of the invention, a method for extracting an analyte across body tissue using electrical current is provided, the improvement comprising transporting at least one background electrolyte (in the opposite direction of the analyte) having a hindrance factor that changes at a faster rate than the hindrance factor of the co-ion of the analyte in the body when an electrical current is applied. The presence of the background electrolyte minimizes changes in analyte flux and reduces intertissue variability.

In yet another aspect of the invention, a method for extracting an analyte across a region of body tissue is provided. First, a reservoir for collection of the analyte and containing at least background ion is placed in contact with the body tissue. The background ion(s) have a hindrance factor that changes at a faster rate than the hindrance factor of the co-ion of the analyte in the body when an electrical current is applied and therefore becomes an ever-increasing competitor for the electrical current as the pore size enlarge. Second, an electrical current of a voltage and duration effective to induce electroporation is applied to the region of body tissue.

BRIEF DESCRIPTION OF THE DRAWINGS

FIG. 1a presents a schematic diagram of iontophoretic drug delivery.

FIG. 1b presents a schematic diagram of analyte extraction. In this case, it is assumed that the analyte is uncharged and is transported by electroosmosis, although this is not necessarily the case.

FIG. 2 illustrates the calculated change in hindrance factor for a permeant ion and sodium ion as a function of changing pore size from 10 to 40 Å. Assumptions made are that the radius of $Na^+$ is 2.5 Å compared with 5.0 Å for the permeant, the permeant has an absolute charge of 1, and the diffusivities of sodium and the permeant are 2.0 and 1.2 $cm^2/s$ respectively.

FIG. 3. graphically depicts the calculated change in transference number for a permeant ion and sodium as a function of changing pore size from 10 to 40 Å. Assumptions made are that the radius of $Na^+$ is 2.5 Å compared with 5.0 Å for the permeant, the permeant has an absolute charge of 1, and the diffusivities of sodium and the permeant are 2.0 and 1.2 $cm^2/s$ respectively.

FIG. 4 is a graphical representation of the calculated change in transference number for a permeant ion, background electrolyte, and sodium as a function of changing pore size from 10 to 40 Å. Assumptions made are that the radii of sodium ion, permeant ion, background electrolyte are 2.5, 5, and 7 Å, respectively, the solution concentrations are 0.1, 0.001, and 0.02 M, respectively and the bulk diffusivities are $2.0 \times 10^{-5}$, $1.2 \times 10^{-5}$, and $0.43 \times 10^{-5}$ $cm^2/sec$, respectively.

FIG. 5 is a graphical representation of the calculated change in the electroosmotic flow hindrance as a function of changing pore size from 10 to 40 Å. It was assumed in calculating the values for this figure that the ionic radius of the permeant is 5 Å.

DETAILED DESCRIPTION OF THE INVENTION

DEFINITIONS AND OVERVIEW

Before describing the present invention in detail, it is to be understood that this invention is not limited to specific drug delivery systems, reverse iontophoresis extraction systems, device structures, enhancers or carriers, as such may vary. It is also to be understood that the terminology used herein is for the purpose of describing particular embodiments only and is not intended to be limiting.

It must be noted that, as used in this specification and the appended claims, the singular forms "a," "an" and "the" include plural referents unless the context clearly dictates otherwise. Thus, for example, reference to "a drug" includes a mixture of two or more drugs, reference to "a co-ion" includes one or more co-ions, reference to "an analyte" includes one or more analytes, and the like.

In describing and claiming the present invention, the following terminology will be used in accordance with the definitions set out below.

Herein the terms "iontophoresis" and "iontophoretic" are used to refer to the transdermal delivery of pharmaceutically active agents by means of an applied electromotive force to an agent-containing reservoir. The terms "iontophoresis" and "iontophoretic" are also meant to refer to "reverse iontophoresis" and "reverse iontophoretic". The terms "reverse iontophoresis", "reverse iontophoretic", and "analyte extraction" are used to refer to the transdermal collection of analytes by means of an applied electromotive force to an analyte-collecting reservoir.

The terms "current" or "electrical current" when used to refer to the conductance of electricity by movement of charged particles is not limited to "direct electrical current", "direct current", or "constant current". The terms "current" or "electrical current" should also be interpreted to include "alternating current", "alternating electrical current", "alternating current with direct current offset", "pulsed alternating current", and "pulsed direct current".

During iontophoresis, certain modifications or alterations of the skin occur and skin permeability changes due to mechanisms such as the formation of transiently existing pores in the skin, also referred to as "electroporation." Any electrically assisted transport of species enhanced by modifications or alterations to the body surface (e.g., formation of pores in the skin and "electroporation") are also included in the term "electrotransport" as used herein. Thus, as used herein, the terms "electrotransport", "iontophoresis" and "iontophoretic" further refer to the transport of permeants by the application of an electric field regardless of the mechanisms.

The term "pore" is used to describe any transport pathway through the tissue, whether formed by electroporation or endogenous to the tissue.

The term "co-ion" is used to define an ion that is transported in the same direction of the active agent in the case of drug delivery or transported in the same direction of the permeant extracted from the body. Other terms that are synonymous with "co-ion" are "background ion", "background electrolyte", and "excipient ion".

The term "permeant" is used to refer to an active agent or an extracted analyte when used in context to drug delivery and analyte extraction respectively. The terms "permeant" and "drug" are interchangeable. The term "permeant" should not be confused to include non-active or non-target extracted substances such as excipient ions or non-target components of body tissues or fluids.

The terms "body surface" and "tissue" are used to refer to skin or mucosal tissue, including the interior surface of body cavities that have a mucosal lining. The term "skin" should be interpreted as including "mucosal tissue" and vice versa.

A "region" of a tissue refers to the area or section of a tissue that is electroporated via the application of one or more electrical signals and through which agent is transported. Thus, a region of a body surface refers to an area of skin or mucosal tissue through which an active agent is delivered or an analyte is extracted.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage., The term "treatment" is also used to refer to the extraction of a substance through a tissue for the purpose of analytical quantitation.

The terms "pharmacologically active agent," "active agent", "pharmaceutical agent," "pharmaceutically active agent", "drug," and "therapeutic agent" are used interchangeably herein to refer to a chemical material or compound suitable for delivery across a tissue (e.g., transdermal or transmucosal administration) and that induces a desired effect. The terms include agents that are therapeutically effective as well as agents that are prophylactically effective. Also included are derivatives and analogs of those compounds or classes of compounds specifically mentioned which also induce the desired effect including active metabolites of the therapeutic agent.

"Vehicles" as used herein refer to carrier materials suitable for administration of an agent across a body surface. Vehicles useful herein include any such materials known in the art that are nontoxic and do not interact with other components of the pharmaceutical formulation or drug delivery system in a deleterious manner. By an "effective" amount (or "therapeutically effective" amount) of a pharmacologically active agent is meant a sufficient, but nontoxic amount of the agent to provide the desired effect. The invention thus provides a method and device for minimizing changes in permeant flux and reducing intertissue variability during iontophoresis.

The following descriptions are offered for the purpose of illustration and not limitation. As depicted in FIG. 1a and FIG. 1b, at physiological pH, the walls of the pores have a net, negative charge density because of the relative excess of aspartic and glutamic amino acids in pore wall proteins. This negative charge causes cations such as sodium ions ($Na^+$), potassium ions ($K^+$), or the like, to be transported from the anode to the cathode. Conversely, for drug delivery (FIG. 1a) drug ions ($D^-$) and background ions ($X^-$) move from the cathode to the anode.

For analyte extraction of positive or neutral permeants (FIG. 1b), the permeant molecule (A) moves with the $Na^+$ ion from the anode to cathode, and the excipient ions ($X^-$) move from cathode to anode. In order to allow for potential reversal of the polarity of the electrodes from time to time, the anode is defined as the electrode with the positive polarity at one instant in time and the cathode is the electrode with the negative polarity at that same instant in time.

All of the descriptions contained herein should not be limited to constant current or direct current methods. All descriptions should also be interpreted to include alternating current or alternating current with direct current offset.

The following equations are used to illustrate this invention. These equations represent thermodynamically ideal situations. Similar calculations can be made for non-ideal situations by using apparent values for physiochemical constants. During constant current (DC), the total electrical current passing through the body tissue ($I_{total}$) is represented by Eq. 1:

$$I_{total=constant}=I_{Na}+I_x+I_P \quad \text{Eq. 1}$$

where
$I_{Na}$, $I_x$, and $I_P$ are defined as the amount of current carried by sodium (Na), the background electrolyte (x), and the drug or permeant (P), respectively. It is obvious to one skilled in the art that $I_{Cl}$, the current carried by the chloride ion, can be substituted for $I_{Na}$ depending on the polarity of the drug.

For a charged permeant, the total amount of permeant transported can be represented by:
Eq. 2

$$J_j = \frac{t_j I_{total}}{z_j F} \quad \text{Eq. 2}$$

where $J_j$ is the flux of the $j$th species, z is the absolute charge on j and F is Faraday's constant.

The current carried by any one ion species, j, is a product of the fraction of current carried by the species (also known as the transference number, t, defined infra) and the total current, as represented by Eq. 3:

$$I_j = t_j I_{total} \quad \text{Eq. 3}$$

Thus, Eqs. 1 and 3 may be rewritten as Eq. 4:

$$I_{total}=constant=[t_{Na}+t_x+t_P]I_{total} \quad \text{Eq. 4}$$

where $t_{Na}$, $t_x$, and $t_P$ are the transference numbers of sodium, background electrolyte, and drug ion, respectively, and the sum of all of the transference numbers equals 1. If the concentration of the co-ion is significantly larger than the concentration of the drug ion, i.e., $C_x >> C_P$, the contribution of the drug ion to the total current is negligible. Therefore, Eq. 4 may be simplified to give Eq. 5:

$$I_{total} \approx [t_{Na}+t_x]I_{total} \quad \text{Eq. 5}$$

The transference number for the sodium ion can be written as Eq. 6:

$$t_{Na} = \frac{C_{Na}D_{Na}H_{Na}z_{Na}^2}{C_x D_x H_x z_x^2 + C_{Na}D_{Na}H_{Na}z_{Na}^2} \quad \text{Eq. 6}$$

where D is a measure of the bulk diffusivities of the ionic species; C is the concentration of the ionic species; and H, the Hindrance Factor, can be defined by Eqs. 6a and 6b as discussed by Deen WM (*AIChE J*; 33:1409–1425, 1987):

$$H=hindrance\ factor=(1-\lambda)^2(1-2.104\lambda+2.09\lambda^3-0.948\lambda^5) \quad \text{Eq. 6a}$$

where $$\lambda = \frac{r}{R} \quad \text{Eq. 6b}$$

where r is the radius of the jth species and R is the pore radius. The hindrance factor has a value between zero and one and decreases when the ratio of permeant size to pore size changes.

Similarly, the transference number for the background co-ion may be expressed by Eq. 7:

$$t_x = \frac{C_x D_x H_x z_x^2}{C_{Na}D_{Na}H_{Na}z_{Na}^2 + C_x D_x H_x z_x^2} \quad \text{Eq. 7}$$

Therefore, again with negligible contribution from the permeant, the total current passing through the tissue may be expressed as a function of the concentration of the jth species, $C_j$, the bulk diffusivities of the jth species, $D_j$, the ionic charge of the species, $z_j$, and the hindrance factor of the species, $H_j$, as shown in Eq. 8.

$$I_{total} = constant \approx \left[\frac{C_{Na}D_{Na}H_{Na}z_{Na}^2}{C_x D_x H_x z_x^2 + C_{Na}D_{Na}H_{Na}z_{Na}^2} + \frac{C_x D_x H_x z_x^2}{C_{Na}D_{Na}H_{Na}z_{Na}^2 + C_x D_x H_x z_x^2}\right] I_{total} \quad \text{Eq. 8}$$

Heretofore, we have discussed only conditions where the contribution of the permeant to the total current is negligible. However, in certain instances, the permeant is present in sufficient concentration to be an important contributor to the total current from the beginning of the treatment. In this instance; equation 8 becomes:

$$I_{total} \approx \begin{bmatrix} \dfrac{C_{Na}D_{Na}H_{Na}z_{Na}^2}{C_PD_PH_Pz_P^2 + C_{Na}D_{Na}H_{Na}z_{Na}^2 + C_xD_xH_xz_x^2} + \\ \dfrac{C_xD_xH_xz_x^2}{C_PD_PH_Pz_P^2 + C_{Na}D_{Na}H_{Na}z_{Na}^2 + C_xD_xH_xz_x^2} + \\ \dfrac{C_PD_PH_Pz_P^2}{C_PD_PH_Pz_P^2 + C_{Na}D_{Na}H_{Na}z_{Na}^2 + C_xD_xH_xz_x^2} \end{bmatrix} I_{total} \qquad \text{Eq. 9}$$

As current causes the average pore size to increase, the contribution of the permeant components to the overall current increases as well. This occurs because the hindrance factor of the larger, more hindered drug molecule increases in an exceedingly rapid manner due to the increased pore size while the hindrance factor of the relatively unhindered sodium ion increases at a much slower rate. FIG. 2 shows the calculated effect on the hindrance factor as the pore size changes using Eqs. 6a and 6b Although the invention will often apply to increases in pore size, it is obvious to one skilled in the art that this invention can be useful for decreasing pore sizes. For example, it is well known that after electroporation, without an external energy force, the transport recover and decrease to their original size. As FIG. 4 shows, this invention can be used to stabilize the change in permeant flux for both increasing and decreasing pore sizes.

Again, assuming that the contribution of the drug to the total current is negligible, the current carried by the permeant may then be expressed using Eq. 10:

$$I_P = \left[ \dfrac{C_PD_PH_Pz_P^2}{C_xD_xH_xz_x^2 + C_{Na}D_{Na}H_{Na}z_{Na}^2} \right] I_{total} \qquad \text{Eq. 10}$$

Due to its larger ionic size, the hindrance factor of the permeant changes at a faster rate than the hindrance factor for sodium during drug delivery. As a consequence, the current carried by the active agent, and therefore active agent flux, changes with time during iontophoresis. FIG. 3 shows the estimated change in transference number with changing pore size as calculated using Eqs. 6 and 7 for a system assumed to contain only the permeant and sodium ($C_x=0$). The graph shows how the relative contribution of the sodium ion to the electrical current transport decreases slightly with increasing pore size while the contribution of the larger species (such as the permeant) changes steeply.

Appropriately chosen background electrolytes can also reduce hindered transport related inter- and intra-skin variability for neutral permeants (e.g. glucose) caused during reverse iontophoresis. For a neutral permeant, the iontophoretic flux ($J_0$) can be expressed by Eqs. 11 and 11a:

$$J_0 = I_t \dfrac{C_0\left(\dfrac{v_0}{E}\right)W_0}{F\sum\limits_{j=1}^{n} C_j\mu_j z_j^2 H_j} \qquad \text{Eq. 11}$$

and $$\mu = \dfrac{DzF}{RT} \qquad \text{Eq. 11a}$$

Where F is Faraday's constant, v is the average velocity of the convective solvent flow (positive v denotes flow from donor to receiver and negative v denotes flow from receiver to donor), $\mu$ is the iontophoretic mobility, T is the absolute temperature, the $_j$ subscripts represent all of the ions transported in the same direction as the permeant, and W is the hindrance factor for pressure-induced parabolic convective solvent flow expressed by.Eq. 12 (Deen 1987):

$$W=(1-\lambda)^2(2-(1-\lambda)^2)(1-0.667\lambda^2-0.163\lambda^3) \qquad \text{Eq.12}$$

FIG. 5 represents the calculated percent change in the convective solvent flow as the pore size changes from 10 to 40 Å assuming a permeant of 5 Å molecular radius and a concentration of 0.00.1 M. As FIG. 5 demonstrates, the electroosmotic hindrance factor changes by over 160% as the pore size change from 10 to 40 Å with greater than a 100% change as the pore size changes from 15 to 25 Å. Since the flux of the permeant is proportional to the hindrance factor, W, it is expected that the permeant flux will vary in a similar manner.

The method of the current invention makes use of a co-ion whose hindrance factor and hence transference number changes faster than those of the permeant, to stabilize the transference number of the permeant. Once the transference number of the permeant is stabilized, the fraction of charge carried by the permeant and, consequently, the permeant flux, is maintained in a constant 'state at constant current, despite changes in the aggregate pore size.

FIG. 4 is a graphical representation, of the calculated influence of the background electrolyte on permeant transference number. In FIG. 4, the influence of an appropriately chosen background electrolyte was calculated into the transference number of the drug and sodium ions. As this graph shows, the presence of the background electrolyte stabilizes the transference number of the drug ion, thereby stabilizing flux during iontophoresis. The calculations used in making FIGS. 2–4 were based on pore size changes from about 10 to 40 Å. The actual change is more likely to be on the order of from about 15 Å to about 25 Å.

As discussed earlier, the method of the invention also minimizes flux variability due to inter-subject pore size differences. The calculations used to construct FIG. 3 show that, for example, a patient with an aggregate pore size of 20 Å has a 112% greater transference number than an individual with an aggregate pore size of 14 Å. On the other hand, when the background co-ion is added to the test solution, the dependence of transport upon patient pore size is mitigated. As FIG. 4 shows, the transference numbers for pores between 14 and 20 Å vary by only 3.8%.

For the purpose of illustration, not limitation, another embodiment of the invention relates to an iontophoretic device for carrying out the aforementioned method, the device comprising first and second electrode assemblies and an electrical current source. The electrode assemblies are adapted to be placed in ion transmitting relation with the body tissue. The first electrode assembly comprises the electrode from which the drug and co-ion are delivered into the body or the background ion delivered and the analyte extracted from the body. The second electrode assembly serves to close the electrical circuit through the body. The circuit is completed by the electrical current source.

In the case of drug delivery, if the drug to be driven into the body is positively charged or uncharged, then the first electrode assembly will comprise the positively charged electrode (the anode) and the second electrode assembly will comprise the negatively charged electrode (the cathode). If the drug to be driven into the body is negatively charged, then the first electrode assembly will be the cathode and the second electrode assembly will be the anode.

In the case of analyte extraction, if the permeant is positively charged or uncharged, then the first electrode assembly will comprise the negatively charged electrode (the cathode) and the second electrode assembly will comprise the positively charged electrode (the anode). If the permeant to be extracted from the body is negatively charged, then the first electrode assembly will comprise the positively charged electrode (the anode) and the second electrode assembly will comprise the negatively charged electrode (the cathode).

Suitable electrode assemblies are well known in the art and any conventional iontophoretic electrode assembly may be used. Suitable electrodes are, for example, disclosed in U.S. Pat. Nos. 4,744,787 to Phipps et al., 4,752,285 to Petelenz et al., 4,820,263 to Spevak et al., 4,886,489 to Jacobsen et al., 4,973,303 to Johnson et al., and 5,125,894 to Phipps et al.

The electrical current may be applied as direct current (DC), alternating current (AC), pulsed DC current, or any combination thereof. Pulsed DC methods are discussed, for example, in U.S. Pat. No. 5,019,034 to Weaver et al. and U.S. Pat. No. 5,391,195 to Van Groningen. Combination pulsed direct current and continuous electric fields are discussed, for example, in U.S. Pat. No. 5,968,006 to Hofmann. U.S. Pat. Nos. 5,135,478 and 5,328,452 to Sabalis, for example, discuss iontophoretic methods that include generating a plurality of waveforms that can be separate or overlapping and that can include an AC signal. U.S. Pat. No. 5,421,817 to Liss et al. discusses the use of a complex set of overlapping waveforms that includes a carrier frequency and various modulating frequencies that collectively are said to enhance: delivery. Co-pending applications "METHODS FOR DELIVERING AGENTS USING ALTERNATING CURRENT" by Li et al., U.S. Provisional No. 60/244,116 filed Oct. 28, 2000 and "METHODS FOR EXTRACTING SUBSTANCES USING ALTERNATING CURRENT" by Li et al., U.S. Provisional No. 60/244,088 filed Oct. 28, 2000, disclose suitable methods of applying AC current alone or in conjunction with a DC prepulse or concomitant DC offset.

The active agent and co-ion will generally be contained in a reservoir connected to the electrode of the first electrode assembly. Suitable reservoir-containing electrode assemblies are disclosed in, for example, U.S. Pat. No. 4,702,732 to Powers et al., U.S. Pat. No. 5,302,172 to Sage, Jr. et al. and U.S. Pat. No. 5,328,455 to Lloyd et al. and will be Well known to those skilled in the art. Examples of such reservoirs or sources include a pouch as described in U.S. Pat. No. 4,250,878 to Jacobsen, a pre-formed gel body as disclosed in U.S. Pat. No. 4,382,529 to Webster and U.S. Pat. No. 4,474,570 to Ariura, et al., a receptacle containing a liquid solution as disclosed in U.S. Pat. No. 4,722,726 to Sanderson et al, a wetable woven or non-woven fabric, a sponge material, or any combination thereof.

It will be appreciated by those working in the field that the present method can be used in conjunction with a wide variety of iontophoretic drug delivery systems systems, as the method is not limited in any way in this regard. Suitable drugs and therapeutic or active agents include any pharmacologically active compound or chemical that is capable of being delivered by iontophoresis, i.e., charged compounds or agents capable of electroosmotic transport. In general, this includes agents in all of the major therapeutic areas including, but not limited to, anti-infectives such as antibiotics and antiviral agents, analgesics including fentanyl, sufentanil, buprenorphine, hydromorphone, and analgesic combinations, anesthetics, anorexics, antiarthritics, antiasthmatic agents such as terbutaline and albuterol, anticonvulsants, antidepressants, antidiabetic agents, antidiarrheals, antihistamines, such as ranitidine, anti-inflammatory agents, antimigraine preparations, antimotion sickness preparations such as scopolamine and ondansetron, antinauseants antineoplastics, antiparkinsonism drugs, antipruritics, antipsychotics, antipyretics, antispasmodics, including gastrointestinal and urinary anticholinergics, sympathomimetrics, xanthine derivatives, cardiovascular preparations including calcium channel blockers such as nifedipine, beta-blockers, beta-agonists such as dobutamine and ritodrine, antiarrhythmics, antihypertensives such as atenolol, ACE inhibitors such as captopril, diuretics, vasodilators, including general, coronary, peripheral and cerebral vasodilators, central nervous system stimulants, cough and cold preparations, decongestants, diagnostics, hormones such as parathyroid hormone, growth hormone, luteinizing hormone, hypnotics, immunosuppressives, muscle relaxants, parasympatholytics, parasympathomimetics, prostaglandins, psychostimulants, sedatives and tranquilizers.

The invention is also useful in conjunction with the iontophoretic delivery of proteins, peptides and fragments thereof, whether naturally occurring, chemically synthesized or recombinantly produced. These substances typically have a molecular weight of at least about 300 daltons, and more typically have a molecular weight of at. least about 300 to 40,000 daltons. Specific examples of peptides and proteins in this size range include, without limitation, LHRH, LHRH analogs such as goserelin, buserelin, gonadorelin, napharelin and leuprolide, GHRH, GHRF, insulin, insultropin, calcitonin, octreotide, endorphin, TRH, NT-36 (chemical name: N-[[(s)-4-oxo-2-azetidinyl]carbonyl]-L-histidyl-L-prolinamide), liprecin, pituitary hormones (e.g., HGH, HMG, desmopressin acetate, etc), follicle luteoids, ANF, growth. factors'such as growth factor releasing factor (GFRF), βMSH, somatostatin, bradykinin, sbmatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, HCG, hirulog, hyaluronidase, interferon, interleukins, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, bradykinin antagonists, CD4, ceredase, CSl's, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 antitrypsin (recombinant), and TGF-beta.

Specific and preferred agents that can be delivered using the present invention include fentanyl hydrochloride, pilocarpine nitrate, lidocaine hydrochloride, hydrocortisone derivatives, sodium salicylate, acetic acid, fluoride anion, lithium, antibiotics such as penicillin and cephalosporin, dexamethasone sodium phosphate, hydromorphone, diazepam salts, antihypertensive agents, bronchodilator agents, peptide hormones and regulatory agents and proteins.

Divalent and polyvalent drugs include, but are not limited to, alniditan, discussed above, as well as talipexole dihydrochloride, carpipramine dihydrochloride, histamine dihydrochloride, proflavine dihydrochloride and gusperimus trihydrochloride.

When applied for the purpose of analyte extraction, the methods disclosed herein can be used in the extraction of a wide range of substances. The methods can generally be utilized to extract any substance that is in a system (e.g., circulatory system) of the subject and that can be transported across a body surface. When the tissue is human skin, the substance is either endogenous or otherwise introduced into the body by some means. Thus, the substance can be molecules that are markers of disease states, pharmaceutical agents administered to the subject, substances of abuse, ethanol, electrolytes, minerals, hormones, peptides, metal ions, nucleic acids, genes, and enzymes or any metabolites, conjugates, or other derivations of the aforementioned products. In some instances, more than one substance can be extracted and monitored at a time.

Substances that can be monitored further include, but are not limited to, oligosaccharides, monosaccharides (e.g., glucose), various organic acids (e.g., pyruvic acid and lactic acid), alcohols, fatty acids, cholesterol and cholesterol-based compounds and amino acids. A number of different substances that correlate with particular diseases or disease states can be monitored. For example, phenylalanine levels can be ascertained to assess treatment of phenylketonuria, which is manifested by elevated blood phenylalanine levels. Examples of metals that can be monitored include, but are not limited to, zinc, iron, copper, magnesium and potassium.

The methods can be utilized to assess the concentration of various pharmacologically active agents that have been administered for either therapeutic or prophylactic treatment. Examples of such substances include, but are not limited to, analeptic agents; analgesic agents; anesthetic agents; antiasthmatic agents; antiarthritic agents; anticancer agents; anticholinergic agents; anticonvulsant agents; antidepressant agents; antidiabetic agents; antidiarrheal agents; antiemetic agents; antihelminthic agents; antihistamines; antihyperlipidemic agents; antihypertensive agents; antiinfective agents; antiinflammatory agents; antimigraine agents; antineoplastic agents; antiparkinsonism drugs; antipruritic agents; antipsychotic agents; antipyretic agents; antispasmodic agents; antitubercular agents; antiulcer agents; antiviral agents; anxiolytic agents; appetite suppressants; attention deficit disorder and attention deficit hyperactivity disorder drugs; cardiovascular agents including calcium channel blockers, antianginal agents, central nervous system ("CNS") agents, beta-blockers and antiarrhythmic agents; central nervous system stimulants; diuretics; genetic materials; hormonolytics; hypnotics; hypoglycemic agents; immunosuppressive agents; muscle relaxants; narcotic antagonists; nicotine; nutritional agents; parasympatholytics; peptide drugs; psychostimulants; sedatives; steroids; smoking cessation agents; sympathomimetics; tranquilizers; vasodilators; β-agonist; and tocolytic agents; or active metabolites thereof.

The background electrolyte or co-ion may be any pharmacologically acceptable electrolyte having a hindrance factor that changes more rapidly than the hindrance factor of the permeant. As discussed above, the hindrance factor for an ion moving through a tissue has been described by Eqs. 6a and 6b $$H = \text{hindrance factor} = (1-\lambda)^2(1-2.104\lambda+2.092\lambda^3-0.948\lambda^5) \quad \text{Eq. 6a}$$

$$\lambda = \frac{r}{R_p} \quad \text{Eq. 6b}$$

where r is the ionic radius of the ion species and R is the pore radius.

As is readily apparent, the rate of change of an ion's hindrance factor is proportional to the ionic radius of the ion, with larger radius ions changing faster in proportion to pore size than smaller radius ions. Therefore, in order to select a background ion having a hindrance factor that changes more rapidly than the hindrance factor of the active agent, one needs to choose an electrolyte having a greater ionic size than the active agent. The choice of background ion is, therefore, dependent upon the desired active agent. Examples of suitable background ions include, but are not limited to polystyrene sulfonate; poly-N-acetylglucosamine; polyadenylic acid; polyadenylic acid-deca-thymidylic acid; polyadenylic acid-dodeca-thymidylic acid; polyadenylic-cytidylic acid; polyadenylic-cytidylic-guanylic acid; polyadenylic-cytidylic-uridylic acid; polyadenylic-guanylic acid; polyadenylic-guanylic-uridylic acid; polyadenylic-polyuridylic acid; polyadenylic-uridylic acid; polyanethole-sulfonic acid; polyanhydrogalacturonic acid; poly-L-arginine; poly-L-asparagine; polybenzylamine acid; polybrene; poly-CBZ-amino acids; polycytidylic acid; poly-cytidylic inosinic acid; polydeoxyadenylic acid; polydeosy-adenylic acid-polythymidylic acid; poly(deoxyadenylic-deoxy-cyticylic)-poly(deoxy-guanylic-thymidylic) acid; polydeoxyadenylic-thymidylic acid; polydeoxycytidylic acid; polydeoxycytidylic-thymidylic acid; polydeoxyguanylic-deoxy-cytidylic acid; polydeoxyguanylic-polydeoxycytidylic acid; polydeoxyinosinic-deoxycytidylic acid; polydeox-ythymidylic acid; polygalacturonic acid; polyglutamic acid; polyguanylic acid; polyguanylic-uridylic acid; polyinosinic acid; polyinosinic-polycytidylic acid; polyinosinic-uridylic acid; polyoxyethylene bis(acetic acid); polythymidylic acid; polyuridylic acid; polyvinyl chloride; polyvinyl sulfate; poly-(α, β)-DL-aspartic acid; poly-L aspartic acid; poly-L-glutamic acid; trisodium timetaphosphate; hexa-ammonium tetrapolyphosphate; pentasodium tripolyphosphate; polyphosphoric acid; dicalcium pyrophosphate; ferric pyrophosphate; tetrapotassium pyrophospahte; disodium pyrophosphate; dextran sulfate, cyclodextran sulfates, or salts or derivatives thereof.

Using the above parameters, one skilled in the art will be able to select a background ion having a larger ionic size than the intended permeant and will be able to determine the concentration of background ion required. One skilled in the art will also recognize that the exact specifications and concentration of the background ion may vary depending upon the desired permeant, its molecular (ionic) size, and its diffusivity.

It is to be understood that while the invention has been described in conjunction with the preferred specific embodiments thereof, the foregoing description, as well as the examples that follow, are intended to illustrate and not limit the scope of the invention. Other aspects, advantages and modifications will be apparent to those skilled in the art to which the invention pertains. All patents, patent applications, journal articles and other references cited herein are incorporated by reference in their entireties.

We claim:

1. An iontophoresis device that minimizes changes in active agent flux and reduces intertissue variability comprising:
   a) a first electrode assembly adapted to be placed in agent transmitting relation with a body tissue comprising
      (i) a pharmacologically active agent to be delivered; and
      (ii) at least one background co-ion having a hindrance factor that changes at a faster rate than the hindrance factor of the active agent when an electrical current is applied;
   b) a second electrode assembly adapted to be placed in ion transmitting relation with the body surface at a location spaced apart from the first electrode assembly; and c) an electrical current source, electrically connected to the first and second electrode assemblies.

2. The device of claim 1, wherein the tissue is skin.

3. The device of claim 1, wherein the tissue is mucosal tissue.

4. The device of claim 1, wherein the background co-ion has an ionic charge that is identical to the ionic charge of the active agent.

5. The device of claim 1, wherein the background co-ion has an ionic charge that exceeds the ionic charge of the active agent.

6. The device of claim 1, wherein the background co-ion has an ionic charge of identical polarity to the active agent.

7. The device of claim 1, wherein the electrical current is direct current.

8. The device of claim 1, wherein the electrical current is alternating current.

9. The device of claim 1, wherein the electrical current comprises both alternating and directed current superimposed over each other.

10. The device of claim 1, wherein the background co-ion has an ionic size effective to minimize changes in active agent flux.

11. The device of claim 1, wherein the pharmacologically active agent is selected from the group consisting of: analeptic agents; analgesic agents; anesthetic agents; antiasthmatic agents; antiarthritic agents; anticancer agents; anticholinergic agents; anticonvulsant agents; antidepressant agents; antidiabetic agents; antidiarrheal agents; antiemetic agents; antihelminthic agents; antihistamines; antihyperlipidemic agents; antihypertensive agents; anti-infective agents; antiinflammatory agents; antimigraine agents; antineoplastic agents; antiparkinsonisrn drugs; antipruritic agents; antipsychotic agents; antipyretic agents; antispasmodic agents; antitubercular agents; antiulcer agents; antiviral agents; anxiolytic agents; appetite suppressants; attention deficit disorder and attention deficit hyperactivity disorder drugs; cardiovascular agents including calcium channel blockers, antianginal agents, central nervous system ("CNS") agents, beta-blockers and antiarrhythmic agents; central nervous system stimulants; diuretics; genetic materials; hormonolytics; hypnotics; hypoglycemic agents; immunosuppressive agents; rimuscle relaxants; narcotic antagonists; nicotine; nutritional agents; parasympatholytics; peptide drugs; psychostimulants; sedatives; steroids; smoking cessation agents; sympathomimetics; tranquilizers; and vasodilators.

12. The device of claim 1, wherein the pharmacologically active agent and the background co-ion are contained in a formulation additionally comprising a vehicle suitable for transdermal drug delivery.

13. The device of claim 1, wherein the first electrode assembly comprises a reservoir electrode adapted to be placed in agent transmitting relation with a body tissue and having a receptacle in which the pharmacologically active agent and the background co-ion are contained.

14. The device of claim 1, wherein said region of tissue has an area in the range of less than approximately 1 cm² to greater than 100 cm².

15. The device of claim 14, wherein the said region of tissue has an area in the range of 5 cm² to 30 cm².

16. The device. of claim 1, wherein the device is suitable for drug delivery that is carried out for a time period in the range of less than 10 minutes to greater than 24 hours.

17. The device of claim 16, wherein the device is suitable for drug delivery that is carried out for a time period in the range of about 1 hour to 12 hours.

18. The device of claim 16, wherein the device is suitable for drug delivery that is carried out for a time period in the range of about 12 hours to 24 hours.

19. In a method for delivering a pharmacologically active.agent across body. tissue using electrical current, the improvement comprising co-delivering with the active agent at least one background co-ion having a hindrance factor that changes at a faster rate than the hindrance factor of the active agent when an electrical current is applied, whereby changes in active agent flux are minimized and intertissue variability is reduced.

20. The method of claim 19, wherein the tissue is skin.

21. The method of claim 19, wherein the tissue is mucosal tissue.

22. A method for delivering a pharmacologically active agent across body tissue, comprising:
(a) placing in contact with the body tissue a composition comprising the pharmacologically active agent and at least one background co-ion having a hindrance factor that changes at a faster rate than the hindrance factor of the active agent when an electrical current is applied; and
(b) applying an electrical current to the region of tissue, the current of a voltage and duration effective to induce electroporation of the body surface in said tissue.

23. The method of claim 22, wherein the tissue is skin.

24. The method of claim 22, wherein the tissue is mucosal tissue.

25. The method of claim 22, wherein the background co-ion has an ionic charge that is identical to the ionic charge of the active agent.

26. The device of claim 22, wherein the background co-ion has an ionic charge that exceeds the ionic charge of the active agent.

27. The device of claim 22, wherein the background co-ion has an ionic charge of identical polarity to the active agent.

28. The method of claim 22, wherein the background co-ion has an ionic radius of at least about 5 angstroms.

29. The method of claim 22, wherein the electrical current is applied as a direct current.

30. The method of claim 22, wherein the electrical current is applied as an alternating current.

31. The method of claim 22, wherein the electrical current is applied as both alternating and direct current superimposed on one another.

32. The method of claim 22, wherein the background co-ion has an ionic size effective to minimize changes in active agent flux.

33. The method of claim 22, wherein the pharmacologically active agent is selected from the group consisting of: analeptic agents; analgesic agents; anesthetic agents; antiasthmatic agents; antiarthritic agents; anticancer agents; anticholinergic agents; anticonvulsant agents; antidepressant agents; antidiabetic agents; antidiarrheal agents; antiemetic agents; antihelminthic agents; antihistamines; antihyperlipidemic agents; antihypertensive agents; anti-infective agents; antiinflammatory agents; antimigraine agents; antineoplastic agents; antiparkinsonism drugs; antipruritic agents; antipsychotic agents; antipyretic agents; antispasmodic agents; antitubercular agents; antiulcer agents; antiviral agents; anxiolytic agents; appetite suppressants; attention deficit disorder and attention deficit hyperactivity disorder drugs; cardiovascular agents including calcium channel blockers, antianginal agents, central nervous system ("CNS") agents, beta-blockers and antiarrhythmic agents; central nervous system stimulants; diuretics; genetic materials; hormonolytics; hypnotics; hypoglycemic agents; immunosuppressive agents; muscle relaxants; narcotic antagonists; nicotine; nutritional agents; parasympatholytics; peptide drugs; psychostimulants; sedatives; steroids; smoking cessation agents; sympathomimetics; tranquilizers; and vasodilators.

34. The method of claim 22, wherein the pharmacologically active agent and the background co-ion are contained in a formulation additionally comprising a vehicle suitable for transdermal drug delivery.

35. The method of claim 22, wherein the pharmacologically active agent and the background co-ion are contained in a receptacle of a reservoir electrode in an iontophoretic drug delivery device, said reservoir electrode being placed in electrical contact with said region of the body surface during steps (a) and (b).

36. The device of claim 22, wherein said region of tissue has an area in the range of less than approximately 1 cm$^2$ to greater than 100 cm$^2$.

37. The device of claim 36, wherein the said region of tissue has an area in the range of 5 cm$^2$ to 30 cm$^2$.

38. The device of claim 22, wherein the device is suitable for drug delivery that is carried out for a time period in the range of less than 10 minutes to greater than 24 hours.

39. The device of claim 38, wherein the device is suitable for drug delivery that is carried out for a time period in the range of about 1 hour to 12 hours.

40. The device of claim 38, wherein the device is suitable for drug delivery that is carried out for a time period in the range of about 12 hours to 24 hours.

41. An iontophoresis device that minimizes changes in permeant flux and reduces intertissue variability comprising:
a) a first electrode assembly adapted to be placed in agent transmitting relation with a body tissue comprising
(i) a reservoir for containing a substance extracted from the body; and
(ii) at least one background ion having a hindrance factor that changes at a faster rate than the hindrance factor of the tissue background ions (the co-ion of the analyte) present in the body when an electrical current is applied;
b) a second electrode assembly adapted to be placed in ion transmitting relation with the body surface at a location spaced apart from the first electrode assembly; and
c) an electrical current source, electrically connected to the first and second electrode assemblies.

42. The device of claim 41, wherein the, tissue is skin.

43. The device of claim 41, wherein the tissue is mucosal tissue.

44. The device of claim 41, wherein the background ion has an ionic charge that is identical to the ionic charge of the co-ion transported with the permeant.

45. The device of claim 41, wherein the background ion has an ionic charge that exceeds the ionic charge of the co-ion transported with the permeant.

46. The device of claim 41, wherein the background ion has an ionic charge of opposite polarity to the co-ion transported with the permeant.

47. The device of claim 41, wherein the electrical current is direct current.

48. The device of claim 41, wherein the electrical current is alternating current.

49. The device of claim 41, wherein the electrical current comprises both alternating and directed current superimposed over each other.

50. The device of claim 41, wherein the background ion has an ionic size effective to minimize changes in permeant extraction through a body surface.

51. The device of claim 41, wherein the extracted substance is glucose.

52. The device of claim 41, wherein the extracted substance is phenylalanine.

53. The device of claim 41, wherein the extracted molecules are markers of disease states, pharmaceutical agents, administered to the subject, substances of abuse, ethanol, electrolytes, minerals, hormones, peptides, metal ions, nucleic acids, genes, enzymes or any metabolites, conjugates, or other derivations of the aforementioned products.

54. The device of claim 41, wherein the extracted permeant is an oligosaccharide, monosaccharide, organic acid, alcohol, fatty acid, cholesterol and cholesterol-based compound, amino acid, zinc, iron, copper, magnesium and potassium.

55. The device of claim 41, wherein the extracted permeant is a pharmacologically active agents that have been administered for either therapeutic or prophylactic treatment, including analeptic agents; analgesic agents; anesthetic agents; antiasthmatic agents; antiarthritic agents; anticancer agents; anticholinergic agents; anticonvulsant agents; antidepressant agents; antidiabetic agents; anrtidiarrheal agents; antiemetic agents; antihelminthic agents; antihistamines; antihyperlipidemic agents; antihypertensive agents; anti-infective agents; antiinflammatory agents; antimigraine agents; antineoplastic agents; antiparkinsonism drugs; antipruritic agents; antipsychotic agents; antipyretic agents; antispasmodic agents; antitubercular agents; antiulcer agents; antiviral agents; anxiolytic agents; appetite suppressants; attention deficit disorder and attention deficit hyperactivity disorder drugs; cardiovascular agents including calcium channel blockers, antianginal agents, central nervous system ("CNS") agents, beta-blockers and antiarrhythmic agents; central nervous system stimulants; diuretics; genetic materials; hormonolytics; hypnotics; hypoglycemic agents; immunosuppressive agents; muscle relaxants; narcotic antagonists; nicotine; nutritional agents; parasympatholytics; peptide drugs; psychostimtilants; sedatives; steroids; smoking cessation agents; sympathomimetics; tranquilizers; vasodilators; β-agonist; and tocolytic agents or metabolites thereof.

56. The device of claim 41, wherein the one or more substance is extracted concomitantly.

57. The device of claim 41, wherein the collection reservoir contains a background ion in a formulation additionally comprising a vehicle suitable for transdermal analyte extraction.

58. The device of claim 41, wherein the first electrode assembly comprises a reservoir electrode adapted to be placed in agent transmitting relation with a body tissue and having a receptacle to collect the target analyte.

59. The device of claim 41, wherein said region of tissue has an area in the range of less than approximately 1 cm$^2$ to greater than 100 cm$^2$.

60. The device of claim 59, wherein the said region of tissue has an area in the range of 5 cm$^2$ to 30 cm$^2$.

61. The device of claim 41, wherein the device is suitable for analyte extraction that is carried out for a time period in the range of less than 10 minutes to greater than 72 hours.

62. The device of claim 61, wherein the device is suitable for analyte extraction that is carried out for a time period in the range of about 1 hour to 12 hours.

63. The device of claim 61, wherein the device is suitable for analyte extraction that is carried out for a time period in the range of about 12 hours to 24 hours.

64. In a method for extracting a permeant across body tissue using electrical current, the improvement comprising transporting, at the same time and in a different direction of the analyte, at least one background ion having a hindrances factor that changes at a faster rate than the hindrance factor of the co-ion of the analyte in the body, whereby changes in permeant flux are minimized and intertissue variability is reduced.

65. The method of claim 64, wherein the tissue is skin.

66. The method of claim 64, wherein the tissue is mucosal tissue.

67. A method for extracting an analyte permeant agent across body tissue, comprising:
   (a) placing in contact with the body tissue a composition comprising at least one background ion having a hindrance factor that changes at a faster rate than the hindrance factor of the co-ion of the analyte in the body when an electrical current is applied; and
   (b) applying an electrical current to the region of tissue, the current of a voltage and duration effective to induce electroporation of the body surface in said tissue.

68. The method of claim 67, wherein the tissue is skin.

69. The method of claim 67, wherein the tissue is mucosal tissue.

70. The device of claim 67, wherein the background ion has an ionic charge that is identical to the ionic charge of the co-ion transported with the permeant.

71. The device of claim 67, wherein the background ion has an ionic charge that exceeds the ionic charge of the co-ion transported with the permeant.

72. The device of claim 67, wherein the background ion has an ionic charge of opposite polarity of the co-ion transported with the permeant.

73. The method of claim 67, wherein the electrical current is applied as a direct. current.

74. The method of claim 67, wherein the electrical current is applied as an alternating current.

75. The method of claim 67, wherein the electrical current is applied as both alternating and direct current superimposed over one another.

76. The method of claim 67, wherein the excipient background ion has an ionic size effective to minimize changes in permeant extraction flux.

77. The method of claim 67, wherein the extracted substance is glucose.

78. The device of claim 67, wherein the extracted substance is phenylalanine.

79. The device of claim 67, wherein the extracted molecules are markers of disease states, pharmaceutical agents administered to the subject, substances of abuse, ethanol, electrolytes, minerals, hormones, peptides, metal ions, nucleic acids, genes, enzymes or any metabolites, conjugates, or other derivations of the aforementioned products.

80. The device of claim 67, wherein the extracted permeant is an oligosaccharide, monosaccharide, organic acid, alcohol, fatty acid, cholesterol and cholesterol-based compound, amino acid, zinc, iron, copper, magnesium and potassium.

81. The device of claim 67, wherein the extracted permeant is a pharmacologically active agents that have been administered for either therapeutic or prophylactic treatment, including analeptic agents; analgesic agents; anesthetic agents; antiasthmatic agents; antiarthritic agents; anticancer agents; anticholinergic agents; anticonvulsant agents; antidepressant agents; antidiabetic agents; antidiarrheal agents; antiemetic agents; antihelminthic agents; antihistamines; antihyperlipidemic agents; antihypertensive agents; anti-infective agents; antiinflammatory agents; antimigraine agents; antineoplastic agents; antiparkinsonism drugs; antipruritic agents; antipsychotic agents; antipyretic agents; antispasmodic agents; antitubercular agents; antiulcer agents; antiviral agents; anxiolytic agents; appetite suppressants; attention deficit disorder and attention deficit hyperactivity disorder drugs; cardiovascular agents including calcium channel blockers, antianginal agents, central nervous system ("CNS") agents, beta-blockers and antiarrhythmic agents; central nervous system stimulants; diuretics; genetic materials; hormonolytics; hypnotics; hypoglycemic agents; immunosuppressive agents; muscle relaxants; narcotic antagonists; nicotine; nutritional agents; parasympatholytics; peptide drugs; psychostimulants; sedatives; steroids; smoking cessation agents; sympathomimetics; tranquilizers; vasodilators; $\beta$-agonist; and tocolytic agents or metabolites thereof.

82. The device of claim 67, wherein the one or more substance is extracted concomitantly.

83. The device of claim 67, wherein the collection reservoir contains a background ion in a formulation additionally comprising a vehicle suitable for transdermal analyte extraction.

84. The device of claim 67, wherein the first electrode assembly comprises a reservoir electrode adapted to be placed in agent transmitting relation with a body tissue and having a receptacle to collect the target analyte and containing the background ion.

85. The device of claim 67, wherein said region of tissue has an area in the range of less than approximately 1 $cm^2$ to greater than 100 $cm^2$.

86. The device of claim 85, wherein the said region of tissue has an area in the range of 5 $cm^2$ to 30 $cm^2$.

87. The device of claim 67, wherein the device is suitable for analyte extraction that is carried out for a time period in the range of less than 10 minutes to greater than 72 hours.

88. The device of claim 87, wherein the device is suitable for analyte extraction that is carried out for a time period in the range of about 1 hour to 12 hours.

89. The device of claim 87, wherein the device is suitable for analyte extraction that is carried out for a time period in the range of about 12 hours to 24 hours.

* * * * *

UNITED STATES PATENT AND TRADEMARK OFFICE
CERTIFICATE OF CORRECTION

PATENT NO. : 6,553,255 B1
DATED : April 22, 2003
INVENTOR(S) : David J. Miller et al.

It is certified that error appears in the above-identified patent and that said Letters Patent is hereby corrected as shown below:

Column 15,
Line 31, please delete "antiparkinsonisrn" and insert -- antiparkisonism --
Line 41, please delete "rimuscle" and insert -- muscle --
Line 59, please delete the "." after "device"

Column 16,
Line 2, please delete the "." between "active"and "agent"
Line 2, please delete the "." between "body"and "tissue"

Column 17,
Line 42, please delete the "," between "the"and "tissue"

Column 18,
Line 2, please delete the "," after "agents"
Line 19, please delete the "anrtidar-" and insert -- "antidar- --
Line 35, please delete the "psychostimtilants" and insert -- psychostimulants --
Line 66, please delete the "hindrances" and insert -- hindrance --

Column 19,
Line 30, please delete the "." between "direct" and "current"

Signed and Sealed this

Fifteenth Day of July, 2003

JAMES E. ROGAN
*Director of the United States Patent and Trademark Office*